| United States Patent [19] | [11] Patent Number: 4,599,339 |
|---|---|
| Nichols et al. | [45] Date of Patent: Jul. 8, 1986 |

[54] USE OF PYRIMIDO[4,5-G]QUINOLINES IN TREATING PARKINSONISM

[75] Inventors: Cynthia L. Nichols; Edmund C. Kornfeld, both of Indianapolis, Ind.

[73] Assignee: Eli Lilly and Company, Indianapolis, Ind.

[21] Appl. No.: 667,307

[22] Filed: Nov. 1, 1984

Related U.S. Application Data

[62] Division of Ser. No. 535,503, Sep. 26, 1983, Pat. No. 4,501,890.

[51] Int. Cl.$^4$ ............................................ A61K 31/505
[52] U.S. Cl. .................................................. 514/267
[58] Field of Search .......................... 514/267; 544/250

[56] References Cited

U.S. PATENT DOCUMENTS

| 4,501,890 | 2/1985 | Nichols et al. | 544/250 |
| 4,507,478 | 3/1985 | Nichols et al. | 544/250 |
| 4,521,421 | 6/1985 | Foreman | 514/267 |

OTHER PUBLICATIONS

Costall and Naylor, *Psychopharmacologia*, 41, 57 (1975).
Bianchine et al., Dopaminergic Mechanisms, *Fed. Proc.*, 37, 2434 (1978).
Post et al., *Arch. Gen. Psychiatry*, 35, 609 (1978).
C. Theohar et al., *Current Therapeutic Research*, 30, 830 (1981).
Randrup et al., *Psychopharmacology*, 53, 309 (1977).

*Primary Examiner*—Mark L. Berch
*Assistant Examiner*—Diana G. Rivers
*Attorney, Agent, or Firm*—Bruce J. Barclay; Arthur R. Whale

[57] ABSTRACT

Trans-($\pm$)-2-Amino or substituted amino-4-permissibly-substituted 6-lower alkyl or allyl-5,5a,-6,7,8,9,9a,10-octahydropyrimido[4,5-g]quinolines, the corresponding trans-($-$)-stereoisomers and salts thereof, useful in treating anxiety, Parkinson's Syndrome, sexual dysfunction, depression, hypertension and elevated prolactin levels, and intermediates useful for the synthesis thereof.

8 Claims, No Drawings

USE OF PYRIMIDO[4,5-G]QUINOLINES IN TREATING PARKINSONISM

This application is a division of application Ser. No. 535,503, filed Sept. 26, 1983, now U.S. Pat. No. 4,501,890.

DESCRIPTION OF THE INVENTION

This invention provides trans-(±)-2,4,6-permissibly substituted-5,5a,6,7,8,9,9a,10-octahydropyrimido[4,5-g]quinolines represented by the formula

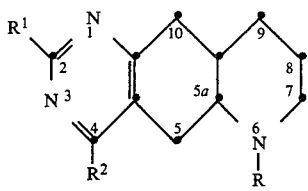

wherein R is H, CN, $C_{1-3}$ alkyl O—CO, $C_{1-3}$ alkyl or allyl; $R^2$ is H, $CH_3$, Cl or Br; $R^1$ is $NH_2$, $NHR^3$ or $NR^4R^5$;

wherein $R^3$ is methyl, ethyl, n-propyl, $C_{1-3}$ alkyl-CO, phenyl-CO or substituted-phenyl-CO wherein said substituents are 1 or 2 members of the group: chloro, fluoro, bromo, methyl, ethyl, methoxy, ethoxy and trifluoromethyl; $R^4$ and $R^5$ are individually methyl, ethyl or n-propyl; and pharmaceutically acceptable acid addition salts thereof.

In the above formula, the term $C_{1-3}$ alkyl includes methyl, ethyl, n-propyl and isopropyl.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Compounds according to I above have two asymmetric carbons (optical centers) at 5a and 9a and can thus exist as four stereoisomers occurring as two racemic pairs, ordinarily designated as the trans-(±) racemate and the cis-(±) racemate. The trans racemate (I) is composed of the trans-(−)-stereoisomer (5aR,9aR stereoisomer) represented by II below and the trans-(+)-(5a,S,9aS stereoisomer) represented by IIa.

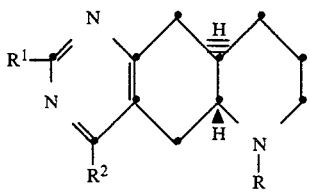

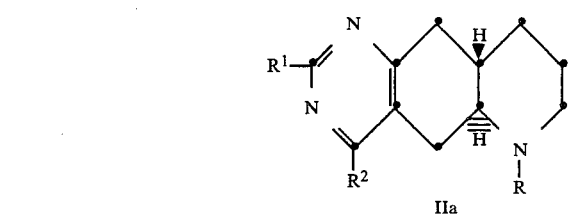

wherein R, $R^1$ and $R^2$ have their previously assigned meanings. These trans-(−)-(5aR,9aR) stereoisomers represented by II are active dopamine agonists and are preferred over the trans-(+)-stereoisomers. Compounds according to II thus form a second aspect of this invention. The trans-(±)-racemates (II+IIa) are chiefly useful for their content of the active trans-(−)-stereoisomer.

Compounds of this invention include illustratively,
5aR,9aR-2-diethylamino-6-ethyl-5,5a,6,7,8,9,9a,10-octahydropyrimido[4,5-g]quinoline sulfate, trans-(±)-2-methylethylamino-4-methyl-6-n-propyl-5,5a,6,7,8,9,9a,10-octahydropyrimido[4,5-g]-quinoline monohydrophosphate, trans-(±)-2-n-propylamino-6-n-propyl-5,5a,6,7,8,9,9a,10-octahydropyrimido[4,5-g]quinoline maleate, 5aR,9aR-2-amino-4-chloro-6-ethyl-5,5a,6,7,8,9,9a,10-octahydropyrimido[4,5-g]quinoline succinate, trans-(±)-2-amino-4-bromo-6-allyl-5,5a,6,7,8,9,9a,10-octahydropyrimido[4,5-g]quinoline phthalate, trans-(±)-2-n-propylamino-6-n-propyl-5,5a,6,7,8,9,9a,10-octahydropyrimido[4,5-g]quinoline mesylate, trans-(±)-2-amino-6-methyl-5,5a,6,7,8,9,9a,10-octahydropyrimido[4,5-g]quinoline hydrochloride 5aR,9aR-2-amino-4-methyl-5,5a,6,7,8,9,9a,10-octahydropyrimido[4,5-g]quinoline tosylate 5aR,9aR-2-acetamido-6-methyl-5,5a,6,7,8,9,9a,10-octahydropyrimido[4,5-g]quinoline dihydrobromide 5aR,9aR-2-benzamido-6-ethyl-5,5a,6,7,8,9,9a,10-octahydropyrimido[4,5-g]quinoline hexan-1,6-dioate trans-(±)-2-n-propylamino-6-isopropyl-5,5a,6,7,8,9,9a,10-octahydropyrimido[4,5-g]quinolinedinitrobenzoate and the like.

Formulas I and II include both active drugs having dopamine agonist activity and intermediates useful in their production. Compounds useful as dopamine agonists are represented by III and IV below

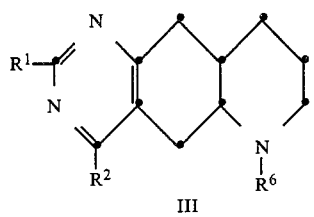

III

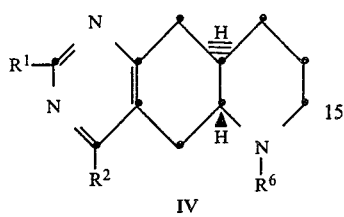

IV wherein $R^6$ is $C_{1-3}$ alkyl or allyl and $R^1$ and $R^2$ have the same meaning as hereinabove.

This preferred group of dopamine agonists are used as drugs either as the free base or as a pharmaceutically-acceptable acid addition salt thereof.

An even more preferred group of compounds are those according to III and IV in which $R^6$ is n-propyl.

Other equally preferred groups of compounds consist of those in which $R^1$ is $NH_2$ and those in which $R^2$ is H.

Compounds represented by Formulas III and IV are dopamine (D-2) agonists substantially devoid of other agonist or antagonist (blocking) activities. As D-2 dopamine agonists, the compounds are useful in treating Parkinson's Syndrome, in treating sexual dysfunction, or as anti-depressants, in lowering blood pressure in hypertensive mammals and in inhibiting prolactin secretion. Thus, other embodiments of this invention include the treatment of hypertension, of depression, of Parkinson's disease and of disease states characterized by an excess of prolactin secretion such as galactorrhea and inappropriate lactation. The use of compounds according to III and IV in treating sexual dysfunction is further elaborated on and claimed in the copending application of Mark Foreman, Ser. No. 535,474, filed this even day now U.S. Pat. No. 4,521,421.

A still further embodiment of this invention is the provision of pharmaceutical formulations for administering drugs according to III and IV in the treatment methods outlined above.

Compounds represented by I–IV above wherein $R^2$ is H are prepared according to the following reaction scheme:

Synthetic Route 1

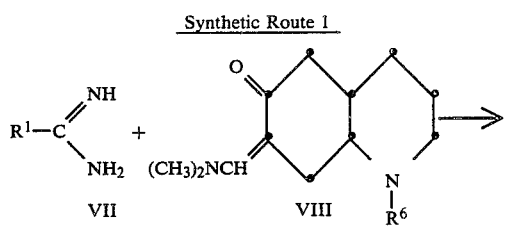

-continued
Synthetic Route 1

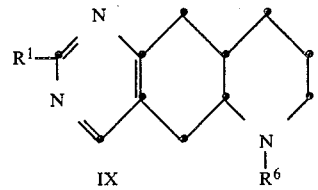

IX wherein $R^1$ and $R^6$ have their previous meanings.

The procedure is equally applicable to the synthesis of the trans-(−)-stereoisomer (IXa),

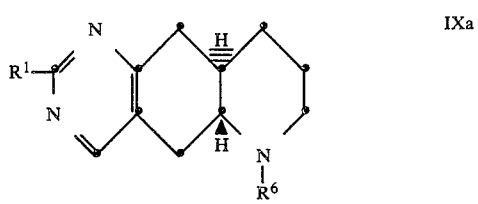

IXa wherein $R^1$ and $R^6$ have the same significance as before. An optically active ketone (Xa below) is used to prepare the optically active intermediate VIIIa

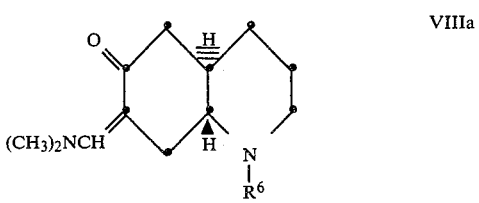

VIIIa wherein $R^6$ has the same significance as before. The preparation of the optically active ketone Xa is described in the copending application of Schaus and Booher, Ser. No. 439,107, filed Nov. 3, 1982 now U.S. Pat. No. 4,471,121, issued Sept. 11, 1984.

A similar synthetic route is used to prepare compounds according to I–IV in which $R^2$ is other than H.

Synthetic Route 2

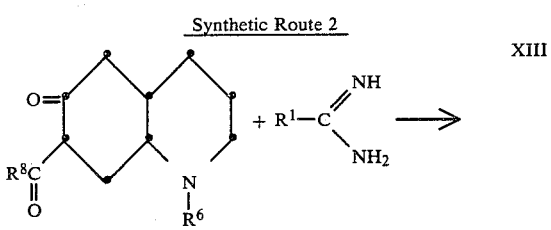

XIII

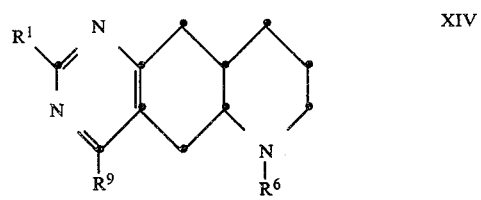

XIV wherein $R^1$ and $R^6$ have their previous significance and $R^8$ is $CH_3$ or $C_{1-3}$ alkyl-O and $R^9$ is $CH_3$ or OH. During the work-up of the ring closure reaction, the $R^8$ of the ester group is replaced with OH to yield a 4-OH derivative. This OH derivative is then halogenated to yield those compounds of this invention where $R^2$ is Cl or Br.

The same procedure starting with the trans-(—)-enantiomer produces XIVa

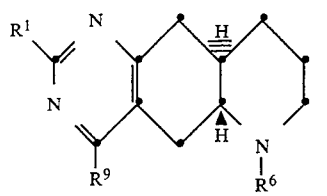

XIVa and this product is transformed where $R^9$ is OH by halogenation to compounds of structure IV.

The starting materials XIII of synthetic route 2 are prepared by the method of Schaus, Huser, and Booher Ser. No. 535,519, filed this even date, now abandoned, continuation application Ser. Nos. 719,041 and 718,761, both filed Apr. 3, 1985. According to this procedure, the ketone (X for the trans racemate, Xa for the trans-(—)-stereoisomer) is metallated at C-7 with a lithium amide as for example lithium diisopropylamide to form an enolate anion. This anion then reacts with acetyl chloride or an dialkylcarbonate to yield those compounds represented by XIII. These latter compounds are transformed to the desired pyrimidine and the pyrimidine purified from isomeric contaminants.

Finally, compounds according to IV or IX are most easily prepared by utilizing a ketone starting material (X or Xa) for the preparation of IX

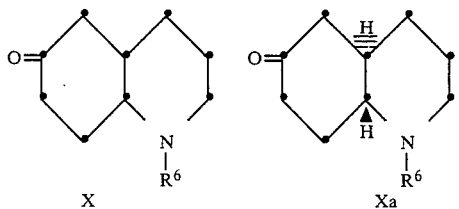

wherein $R^6$ is $C_{1-3}$ alkyl or allyl. The ketones represented by X or Xa, when $R^6$ is $C_{1-3}$ alkyl, are preferably prepared by the method of Schaus, Ser. No. 384,817, filed June 2, 1982, now abandoned, but subject matter maintained in continuation-in-part application Ser. No. 521,863, filed Aug. 10, 1983, now U.S. Pat. No. 4,540,787 whereby a 6-alkoxyquinoline of the formula

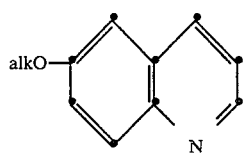

XI is quaternized with a $C_{1-3}$ alkyl halide and the quaternized salt reduced to yield an N-$C_{1-3}$ alkyl 6-alkoxy-1,2,3,4-tetrahydroquinoline of the formula

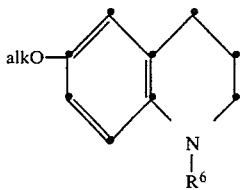

XIa wherein $R^6$ is $C_{1-3}$ alkyl. The particular $C_{1-3}$ alkyl group remains intact through the next two reduction steps: a Birch reduction followed by a sodium cyanoborohydride or borohydride reduction to yield, ultimately, an octahydroquinoline of the formula XII

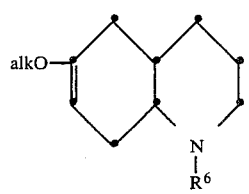

XII wherein $R^6$ is $C_{1-3}$ alkyl. This enol ether yields X upon treatment with acid. Xa is then produced by resolution of X as previously set forth.

Compounds according to III or IV in which $R^6$ is allyl are prepared by a different procedure which will be described below.

The ketones X or Xa are readily transformed by treatment with dimethylformamide dimethylacetal to yield VIII or VIIIa, the starting materials of Synthetic Route 1.

An alternative preparation of the ketone X, when $R^6$ is $C_{1-3}$ alkyl, is set forth in U.S. Pat. Nos. 4,198,415, cols. 4-5 (the ketone as VII and the dimethylamino methylene derivative VIII in that reaction scheme.)

An alternative intermediate to VIII or VIIIa, a 1-alkyl-6-oxo-7-formyldecahydroquinoline, is disclosed in Schaus, Ser. No. 438,834 filed Nov. 3, 1982, now abandoned, but subject matter maintained in continuation-in-part application Ser. No. 636,959, filed Aug. 2, 1984, as is the method of preparing this intermediate from the 6-oxo derivative (X or Xa).

The intermediates VIII or VIIIa can also be prepared by treating the above 1-alkyl-6-oxo-7-formyldecahydroquinoline of Schaus (loc. cit.) with dimethyl amine in the presence of a dehydrating agent to yield the 7-dimethylaminomethylene derivative.

As can be seen from the above discussion, the group $R^6$ in formula X carries through the synthetic procedure intact. Thus, if it is desired to replace one alkyl group with another or with allyl, indirect synthetic routes must be used. For example, if $R^6$ in X or Xa is methyl or n-propyl, reaction with cyanogen bromide yields a 1-cyano-6-oxodecahydroquinoline XV or XVa where $R^7$ is cyano. Hydrolysis of the cyano group yields the secondary amine, XV or XVa, where $R^7$ is H. Similarly, reaction of X or Xa where $R^6$ is methyl with ethyl chloroformate yields an intermediate, XV or XVa, wherein $R^7$ is $C_2H_5$—O—CO, which can also be hydrolyzed to yield the corresponding compound XV or XVa wherein $R^7$ is H.

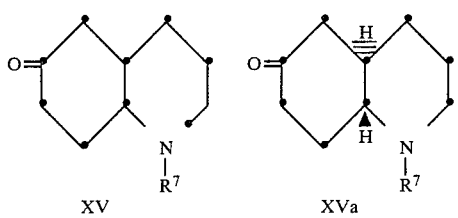

The secondary amine XV or XVa where $R^7$ is H can then be selectively alkylated, with the same or different alkyl group, or can be allylated where it is desired to have an allyl group on the ring nitrogen. In this synthesis, the extremely reactive allyl halides can be used to ultimately yield X or Xa where $R^6$ is allyl.

Again alternatively, XV or XVa in which $R^7$ is CN can be reacted with guanidine to yield a novel intermediate according to I or II where $R^1$ is $NH_2$, $R^2$ is H and R is CN (XVI and XVIa):

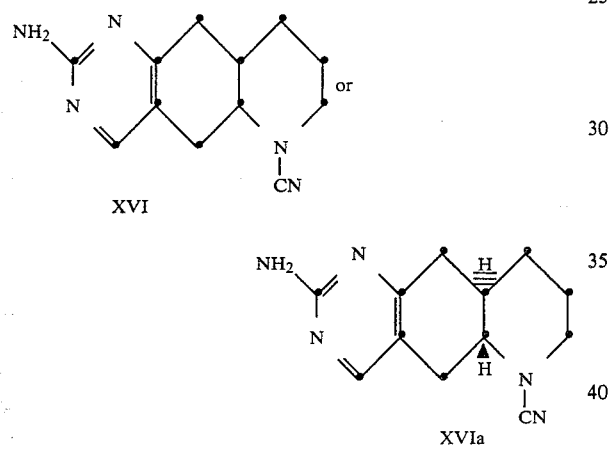

Hydrolysis of the cyano product yields compounds according to I or II in which R and $R^2$ are both H and R is $NH_2$. Such compounds can then be selectively alkylated or allylated to yield drugs of formulas III and IV where $R^1$ is $NH_2$, $R^2$ is H and $R^6$ is as defined. This procedure is also a neat method for introducing a tagged carbon into the $R^6$ group at a late stage in the synthesis so as to avoid carrying the expensive (isotopic or radioactive) tagged molecule through several synthetic procedures with consequent loss of yield.

One still further synthetic route is available for preparing drugs in which $R^6$ is allyl. This route involves adapting the Kornfeld-Bach synthesis disclosed in U.S. Pat. No. 4,198,415, Reaction Scheme I. By using an allyl halide in step 2 of the procedure of that patent, a trans-($\pm$)-1-allyl-6-oxodecahydroquinoline (VIII in the reaction Scheme) is produced. This N-allyl derivative is then converted to trans-($\pm$)-1-allyl-6-oxo-7-dimethylaminomethylenedecahydroquinoline, formula VIII wherein $R^6$ is allyl. The trans-($\pm$)enantiomer can then be produced from the racemate by resolution.

Compounds according to I or II and III or IV in which $R^1$ is $NHR^3$, $R^2$ is H, $CH_3$, Cl or Br, and $R^3$ is $C_{1-3}$ alkyl-CO or permissibly-substituted phenyl-CO are prepared by acylating IX (or the 5aR,9aR stereoisomer) when $R^1$ is $NH_2$ with an acid chloride or anhydride under standard reaction conditions.

Finally, there are two methods of providing the trans-($\pm$) or 5aR, 9aR derivatives, II or IV. The first method is the resolution of the trans-($\pm$) racemate (I, III) using a resolving agent such as d-(—)-S-tartaric acid or other suitable optically-active acid which forms a salt with the trans-(—) component of trans-($\pm$)-2-substituted-6-$C_{1-3}$ alkyl (allyl)-5,5a,6,7,8,9,9a,10-octahydropyrimido[4,5-g]quinoline (IV). Preferably, however, a resolution is carried out on the bicyclic ketone, X or XV, to produce a 4aR,8aR-1-alkyl (or allyl)-6-oxodecahydroquinoline, according to the procedure of Schaus and Booher, Ser. No. 439,107 filed Nov. 3, 1982, now U.S. Pat. No. 4,471,121, issued Sept. 11, 1984. The resolved ketone can then be reacted with dimethylformamide dimethylacetal or with ethyl formate followed by $(CH_3)_2NH$ to yield 4aR,8aR-1-alkyl (or allyl)-6-oxo-7-dimethylaminomethylenedecahydroquinoline of the formula

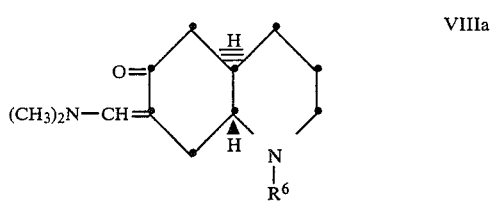

wherein $R^6$ has its previously assigned meaning. VIIIa can then be reacted with

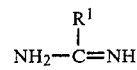

to yield the optically-active derivative IV directly or indirectly.

This invention is further illustrated by the following specific examples.

EXAMPLE 1

Preparation of trans-($\pm$)-2-amino-6-methyl-5,5a,6,7,8,9,9a,10-octahydropyrimido[4,5-g]quinoline A reaction mixture was prepared from 1.8 g. of trans-($\pm$)-1-methyl-6-oxodecahydroquinoline and 2.2 g. of tris-dimethylaminomethane in 18 ml. of toluene. The reaction mixture was refluxed under nitrogen for about 12 hours. An additional 0.8 g. of tris-dimethylaminomethane were added and refluxing continued under nitrogen for an additional 5 hours. The reaction mixture was then concentrated to dryness in vacuo. The resulting residue containing trans($\pm$)-1-methyl-6-oxo-7-(dimethylaminomethylene)decahydroquinoline formed in the above reaction was dissolved in 40 ml. of ethanol to which was added 1.5 g. of guanidine carbonate. The resulting mixture was heated overnight to reflux temperature under a nitrogen atmosphere. On cooling, a crystalline precipitate formed which was collected by filtration and the filter cake washed with ethanol; yield=0.68 g. of a light yellow powder. The material was dissolved in 1N aqueous hydrochloric acid. The acidic solution was then made basic with 10% aqueous sodium hydroxide. Trans-(±)-2-amino-6-methyl-5,5a,6,7,8,9,9a,10-octahydropyrimido[4,5-g]quinoline free base, being insoluble in the alkaline layer, separated and was extracted with chloroform. The chloroform extract was dried and the chloroform removed in vacuo. The residue, comprising trans-(±)-2-amino-6-methyl-5,5a,6,7,8,9,9a,10-octahydropyrimido[4,5-g]quinoline was suspended in ethanol and the ethanol solution saturated with gaseous hydrogen chloride. The solvent was removed in vauco and the resulting residue, the dihydrochloride salt of trans-(±)-2-amino-6-methyl-5,5a,6,7,8,9,9a,10-octahydropyrimido[4,5-g]quinoline, was recrystallized from hot ethanol. Sixty-six mg. of dihydrochloride salt were obtained having the following analysis (after drying at 150° C.):

Theory: C, 49.49; H, 6.92; N, 19.24. Found: C, 49.61; H, 7.03; N, 18.92.

The higher temperature drying was necessary because it became apparent after drying at lower temperatures that the dihydrochloride salt crystallizes as a solvate and the solvent must be removed by drying to obtain a reproducible analysis.

The above reaction was repeated except that 1 g. of trans-(±)-1-n-propyl-6-oxo-7-dimethylaminomethylenedecahydroquinoline was reacted with 0.4 g. of guanidine carbonate in 20 ml. of anhydrous ethanol. (Trans-(±)-1-n-propyl-6-oxo-7-dimethylaminomethylenedecahydroquinoline was prepared from trans-(±)-1-n-propyl-6-oxodeachydroquinoline and tris-dimethylaminomethane according to the above procedure). The reaction mixture was heated under reflux temperature overnight at which time a precipitate was observed. The reaction mixture was chilled in an ice bath and a light yellow crystalline precipitate comprising trans-(±)-2-amino-6-n-propyl-5,5a,6,7,8,9,9a,10-octahydropyrimido[4,5-g]quinoline formed in the above reaction was collected. The filter cake was washed with ethanol and then dried; m.p. =above 260° C.

Analysis calculated: C, 68.26; H, 9.00; N, 22.74. Found: C, 68.45; H, 8.87; N, 22.26.

Trans-(±)-2-amino-6-n-propyl-5,5a,6,7,8,9,9a,10-octahydropyrimido[4,5-g]quinoline was dissolved in 1N aqueous hydrochloric acid and the acidic solution extracted with ether. The acidic solution was then made basic with 10% aqueous sodium hydroxide. Trans-(±)-2-amino-6-n-propyl-5,5a,6,7,8,9,9a,10-octahydropyrimido[4,5-g]quinoline precipitated and was separated by filtration. Six-tenths grams of trans-(±)-2-amino-6-n-propyl-5,5a,6,7,8,9,9a,20-octahydropyrimido[4,5-g]quinoline were obtained. The free base was again dissolved in 1N aqueous hydrochloric acid, and the water removed in vacuo. The resulting residue was recrystallized from hot ethanol. Trans-(±)-2-amino-6-n-propyl-5,5a,6,7,8,9,9a,10-octahydropyrimido[4,5-g]quinoline dihydrochloride thus prepared had the following analysis.

Analysis calculated for $C_{14}H_{22}N_4.2HCl.H_2O$ C, 49.74; H, 7.75; N, 16.57; Cl, 20.97; Found: C, 49.88; H, 8.03; N, 16.81; Cl, 20.87.

After drying at 120° C., analysis indicated that water of hydration and one-half mole of hydrogen chloride had been lost to yield trans-(±)-2-amino-6-n-propyl-5,5a,6,7,8,9,9a,10-octahydropyrimido-[4,5-g]quinoline sesquihydrochloride having the following analysis.

Analysis calculated for $C_{14}H_{22}N_4.1.5$ HCl C, 55.86; H, 7.87; N, 18.61; Cl, 17.03 Found: C, 55.49; H, 7.83; N, 18.35; Cl, 17.03.

EXAMPLE 2

Preparation of Trans-(±)-2-acetylamino-6-n-propyl-5,5a,6,7,8,9,9a,10-octahydropyrimido[4,5-quinoline A solution was prepared containing 0.75 g of trans-(±)-2-amino-6-n-propyl-5,5a,6,7,8,9,9a,10-octahydropyrimido[4,5-g]quinoline in 20 ml. of pyridine and 0.34 g. of acetic anhydride was added thereto in dropwise fashion. The reaction mixture was heated to reflux temperature under a nitrogen blanket overnight. TLC at this point in time indicated that starting material was still present; therefore, about 1.5 ml. more acetic anhydride were added and the reaction mixture again heated to reflux temperature under a nitrogen blanket. TLC, using a 9:1 chloroform/methanol solvent system containing ammonia, indicated that the reaction had gone largely toward completion but that some starting material was still present. The reaction mixture was therefore concentrated in vacuo and the resulting residue triturated in hot ethyl acetate. On cooling, crystals formed which were isolated by filtration. Thirty-four hundredths grams of trans-(±)-2-acetylamino-6-n-propyl-5,5a,6,7,8,9,9a,10-octahydropyrimido[4,5-g]quinoline were obtained; molecular ion at 288; nmr and infrared spectra were in comformance with the proposed structure.

Following the above procedure, trans-(±)-2-amino-6-n-propyl-5,5a,6,7,8,9,9a,10 -cotahydropyrimido[4,5-g]quinoline was reacted with benzoyl chloride in pyridine solution. The residue obtained after working up the reaction mixture as indicated above was chromatographed over florisil using chloroform with increasing amounts (0–10%) of methanol as the eluant. Fraction ten contained the desired 2-benzoylamino compound (by TLC). The solvent was removed therefrom in vacuo. The resulting residue was dissolved in ethanol and gaseous hydrogen chloride passed into the ethanol solution. Addition of ether to the point of incipient precipitation yielded trans-(±)-2-benzoylamino-6-n-propyl-5,5a,6,7,8,9,9a,10-octahydropyrimido[4,5-g]quinoline dihydrochloride; molecular ion at 350.

Analysis (after drying at 130° C.) C, 159.57; H, 6.67; N, 13.23 Found: C, 59.35; H, 6.85; N, 12.99.

EXAMPLE 3

Preparation of 5aR,9aR-2-Amino-6-n-propyl-5,5a,6,7,8,9,9a,10-octahydropyrimido[4,5-g]quinoline Following the procedure of Example 1, 4aR,8aR-1-n-propyl-6-oxo-7-dimethylaminomethylenedecahydroquinoline (prepared from 4aR,8aR-1-n-propyl-6-oxodecahydroquinoline and tris-dimethylaminomethane) was reacted with guanidine carbonate in anhydrous ethanol solution. The reaction was carried out and the reaction mixture worked up as in Example 1 to yield 2.4 g. of 5aR,9aR-2-amino-6-n-propyl-5,5a,6,7,8,9,9a,10-octahydropyrimido[4,5-g]quinoline.

The product was suspended in ethanol and gaseous hydrogen chloride bubbled through the suspension. The resulting solution was evaporated to dryness in vacuo and the residual yellow oil dissolved in a small amount of ethanol (about 10 cc). Ether was added to the point of incipient precipitation and the mixture heated on the steam bath. Upon cooling, fine, powdery crystals formed which were separated by filtration. The filter cake was washed with ethanol to yield 0.72 g. of the dihydrochloride salt of 5aR,9aR-2-amino-6-n-propyl-5,5a,6,7,8,9,9a,10-octahydropyrimido[4,5-g]quinoline.

Analysis (after drying at 180° C.) C, 52.67; H, 7.58; N, 17.55 Found: C, 52.81; H, 7.75; N, 17.65.

Molecular ion at 246; Optical rotation $[\alpha]_{589}^{25°\,C.} = -99.6°$; $[\alpha]_{360}^{25°\,C.} = -374.8°$

EXAMPLE 4

Preparation Trans-($\pm$)-2-dimethylamino-6-n-propyl-5,5a,6,7,8,9,9a,10-octahydropyrimido[4,5-g]quinoline A reaction mixture was prepared from 4.7 g. of trans-($\pm$)-1-n-propyl-6-oxo-7-dimethylaminomethylenedecahydroquinoline and 2.5 g. of 1,1-dimethylguanidinehydrochloride in 50 ml. of anhydrous ethanol. The reaction mixture was heated overnight under a nitrogen atmosphere, and was then cooled and the volatile constituents removed in vacuo. The resulting residue was dissolved in ethyl acetate and the ethyl acetate solution contacted with an excess of 10% aqueous sodium hydroxide. Trans-($\pm$)-2-dimethylamino-6-n-propyl-5,5a,6,7,8,9,9a,10-octahydropyrimido[4,5-quinoline formed in the above reaction, being insoluble in the basic layer, remained in the ethyl acetate layer. The aqueous layer was separated and the ethyl acetate layer extracted once with water and once with saturated aqueous sodium chloride. The ethyl acetate layer was dried and the ethyl acetate removed in vacuo to leave 0.75 g. of an orange oil. The oily residue was chromatographed over florisil using hexane containing increasing amounts (1–50%) of ethyl acetate as the eluant. Fractions shown by TLC to contain the desired trans-($\pm$)-2-dimethylamino-6-n-propyl-5,5a,6,7,8,9,9a,10-octahydropyrimido[4,5-g]quinoline were combined and the solvent removed from the combined fractions in vacuo. The resulting residue was dissolved in ethanol and gaseous hydrogen chloride passed into the solution thus forming the corresponding dihydrochloride salt. The ethanol was removed therefrom in vacuo and the dihydrochloride salt crystallized from a methanol-ethyl acetate solvent mixture to yield 0.170 g. of a white solid having a molecular ion at 274.

Analysis calculated: C, 55.33; H, 8.13; N, 16.13 Found: C, 55.67; H, 8.19; N, 16.19.

Following the above procedure, but substituting N-methylguanidine for N,N-dimethylguanidine, trans-($\pm$)-2-methylamino-6-n-propyl-5,5a,6,7,8,9,9a,10-octahydropyrimido[4,5-g]quinoline was prepared. The compound was purified by chromatography over florisil using methylene dichloride containing increasing (0–10%) methanol as the eluant; yield=0.66 g. The monohydrochloride salt was prepared by adding an equivalent of 0.1N hydrochloric acid to the solid and recrystallizing the product from methanol; yield=599 mg.

Analysis calculated: C, 60.69; H, 8.49; N, 18.87; Cl, 11.94 Found: C, 60.96; H, 8.53; N, 19.07; Cl, 11.74.

In Examples 1–2 and 4, the optically active 5aR,9aR derivative can be prepared from the desired 4aR,8aR-1-C$_{1-3}$-alkyl-6-oxo-7-dimethylaminomethylene decahydroquinoline and a suitable guanidine.

EXAMPLE 5

Preparation of trans-($\pm$)-2-Amino-4-methyl-6-n-propyl-5,5a,6,7,8,9,9a,10-octahydropyrimido[4,5-g]quinoline Following the procedures of Schaus, Huser, and Booher, (loc. cit) a reaction mixture was prepared by adding 13.7 ml. of 1.6M n-butyllithium in hexane to a solution containing 3.1 ml. of diisopropylamine and 22 ml. of THF at about 0° C. under a nitrogen atmosphere. The reaction mixture was stirred for about 30 minutes. Next, 2.0 g. of trans-($\pm$)-1-n-propyl-6-oxodecahydroquinoline in a small amount of THF was added while containing the reaction mixture at about −78° C. The solution was stirred for two hours at which time 1.1 ml. of acetyl chloride was added. This new reaction mixture was stirred at about −78° C. for about 30 minutes and then at room temperature for two hours. The reaction mixture was next poured into water and the consequent aqueous mixture acidified to a pH=9–10 with 1N aqueous hydrochloride acid. The aqueous solution was extracted three times with equal volumes of methylene dichloride. The methylene dichloride extracts were combined and the combined extracts dried. Evaporation of the solvent yielded 2.7 g. of trans-($\pm$)-1-n-propyl-6-oxo-7-acetyldecahydroquinoline. The crude reaction product (without further purification) was mixed with about 0.9 g. of guanidine carbonate. Forty ml. of ethanol were added and the reaction mixture refluxed under a nitrogen atmosphere. The reaction mixture was then evaporated to dryness and the crude product chromatographed over florisil. Fractions shown to contain trans-($\pm$)-2-amino-4-methyl-6-n-propyl-5,5a,6,7,8,9,9a,10-octahydropyrimido[4,5-g]quinoline formed in the above reaction were combined to yield 270 mg of free base, and 10 ml. of 0.1N aqueous hydrochloric acid were added thereto. The hydrochloride salt thus formed was recrystallized from ethanol; m.p.=above 240° C.; mass spectrum molecular ion at 260, small peak at 268.

Analysis Calculated: C, 54.05; H, 7.86; N, 16.81; Found: C, 53.93; H, 7.98; N, 16.61.

EXAMPLE 6

Preparation of trans-(±)-2-Amino-4-chloro-6-n-propyl-5,5a,6,7,8,9,9a,10-octahydropyrimido[4,5-g]quinoline A reaction mixture was prepared from 2.0 g. of trans-(±)-1-n-propyl-6-oxo-7-ethoxycarbonyldecahydro quinoline (prepared by the method of Schaus, Huser, and Booher—loc. cit.), 20 ml. of anhydrous ethanol and 0.67 g. of guanidine carbonate. The reaction mixture was heated to reflux temperature overnight under a nitrogen atmosphere. The white precipitate which formed was collected by filtration and the filter cake washed with ethanol and dried; yield=1.36 g. The filter cake was dissolved in 52 ml. of 0.1N aqueous hydrochloric acid. The acidic mixture was filtered and the filtrate concentrated in vacuo. The solid residue was dissolved in boiling methanol. The methanol solution was filtered and trans-(±)-2-amino-4-hydroxy-6-n-propyl-5,5a,6,7,8,9,9a,10-octahydropyrimido[4,5-g]quinoline hydrochloride thus prepared crystallized to yield 0.79 g. of product. The free base had the following physical characteristics: mass spectrum, molecular ion at 262.

Analysis Calculated: C, 64.08; H, 8.45; N, 21.36; Found: C, 64.18; H, 8.51; N, 21.13.

The hydrochloride salt had the following physical characteristics: mass spectrum, molecular ion at 262.

The 4-hydroxy product thus obtained was refluxed with 4 ml. of phosphorous oxychloride. The reaction mixture, containing trans-(±)-2-amino-4-chloro-6-n-propyl-5,5a,6,7,8,9,9a,10-octahydropyrimido[4,5-g]quinoline formed in the above reaction, was poured onto ice and the resulting aqueous mixture made basic. The basic mixture was filtered and the insoluble material dissolved in 0.1N aqueous hydrochloric acid. The hydrochloride salt thus prepared was recrystallized from ethanol to yield trans-(±)-2-amino-4-chloro-6-n-propyl-5,5a,6,7,8,9,9a,10-octahydropyrimido[4,5-g]quinoline hydrochloride having the following physical characteristics. Mass spectrum, molecular ion at 280, smaller peak at 282.

Analysis Calculated: C, 53.00; H, 6.99; N, 17.66; Found: C, 53.15; H, 6.92; N, 17.77.

The 4-bromo derivative can be made similarly by substituting PBr$_3$ for POCl$_3$ in the above reaction.

The 4aR,8aR-1-substituted-6-oxodecahydroquinoline used to prepare the 7-dimethylaminomethylene starting material of Example 3 is itself prepared as follows. (The 1-n-propyl derivative is illustrated for purposes of exemplification only. Other 1-alkyl, allyl or benzyl derivatives can be resolved in similar fashion).

PREPARATION 1

Ten g. of (−)-di-p-toluoyltartaric acid were dissolved in 75 ml. of warm methanol. The solution was added to a solution of 5.05 g. of trans-dl-1-n-propyl-6-oxodecahydroquinoline in 15 ml. of methanol. The reaction mixture was brought to a boil and was then allowed to cool to ambient temperature. After remaining at ambient temperature overnight, crystallization was induced by the addition of seed crystals previously obtained. The crystalline tartarate salt was isolated by filtration and the filter cake washed with methanol; yield=2.813 g. (18.7%) of a white crystalline solid comprising the (−)-di-p-toluoyltartrate of 4aR,8aR-1-n-propyl-6-oxodecahydroquinoline; $[\alpha]_D^{25°} = -107.49°$ (MeOH, c=1). Recrystallization of the salt from methanol gave 1.943 g. of the optically pure salt, $[\alpha]_D^{25°} = -108.29°$ (MeOH, c=1). The (−)-di-p-toluoyltartrate salt thus obtained was treated with dilute aqueous sodium hydroxide and the resulting alkaline solution extracted with methylene dichloride. The methylene dichloride extract was dried, concentrated and the solvent removed therefrom in vacuo. The resulting residue was distilled to yield a colorless oil comprising purified 4aR,8aR-1-n-propyl-6-oxodecahydroquinoline; $[\alpha]_D^{25°} = -88.51°$ (MeOH, c=1).

Other 1-substituted (C$_{1-3}$ alkyl, H, CN, benzyl or alkyl)-6-oxodecahydroquinolines can be resolved in similar fashion.

The preparation of other useful intermediates are illustrated in the following preparations.

PREPARATION 2

Preparation of trans-(±)-1-n-propyl-6-oxo-7-dimethylaminomethylenedecahydroquinoline Four grams of trans-(±)-1-n-propyl-6-oxodecahydroquinoline were added to a solution of 5.6 g. of potassium t-butoxide in about 50 ml. of anhydrous redistilled tetrahydrofuran. The reaction mixture was stirred for 30 minutes under a nitrogen atmosphere. Next, 3.6 ml. of ethyl formate were added in dropwise fashion while the reaction mixture was cooled in an ice-alcohol bath. After the addition had been completed, the reaction mixture was stirred at ambient temperature under a nitrogen atmosphere overnight. The reaction mixture, at this point a solid slurry, was neutralized with glacial acetic acid. Methanol was added to the slurry, followed by 1 ml. of dimethylamine. A molecular sieve was added to aid dehydration. The subsequent reaction mixture was stirred under a nitrogen atmosphere for 48 hours, and was then filtered. The filtrate was evaporated to dryness in vacuo. Water was added and the aqueous mixture extracted three times with equal volumes of methylene dichloride. The methylene dichloride extracts were combined and the combined extracts washed with water and then dried. Evaporation of the methylene dichloride yielded 4.15 g. (81.4%) yield of trans-(±)-1-n-propyl-6-oxo-7-dimethylaminomethylenedecahydroquinoline.

PREPARATION 3

Preparation of trans-(±)-2-amino-6-cyano-5,5a,6,7,8,9,9a,10-octahydropyrimido[4,5-g]quinoline A reaction mixture was prepared from 16 g. of trans-(±)-1-methyl-6-oxodecahydroquinoline prepared by the procedure of Bach and Kornfeld (loc. cit.), 26 g. of cyanogen bromide and 450 ml. of methylene dichloride. The reaction mixture was stirred overnight at room temperature and was then extracted three times with 1N aqueous hydrochloric acid. The acid extracted reaction mixture was washed with saturated aqueous sodium bicarbonate and then dried. Any volatile material were removed by evaporation in vacuo. The residue thus obtained was 18.8 g. of a semi-solid oil comprising trans-(±)-1-cyano-6-oxodecahydroquinoline formed in the above reaction. Chromatography of the oil over florisil using chloroform as the eluant yielded fractions of purified material weighing collectively 11.5 g. (66%) yield. The oil crystallized upon standing to yield white crystals.

A reaction mixture was prepared from 4.18 g. of trans-(±)-1-cyano-6-oxodecahydroquinoline, 5.0 g. of tris-dimethylaminomethane and 50 ml. of toluene. The reaction mixture was refluxed under nitrogen temperature for five hours and then was concentrated in vacuo. Five and seventy-six hundredths grams of a crude yellow solid comprising trans-(±)-1-cyano-6-oxo-7-dimethylaminomethylenedecahydroquinoline were obtained. This crude product was mixed with 2.25 g. of guanidine carbonate in 100 ml. of anhydrous methanol. This reaction mixture was heated to reflux under nitrogen overnight, and was then concentrated in vacuo. The resulting solid residue was triturated with hot methanol and filtered. The filter cake was washed twice with methanol and once with ether. A yield of 4.11 g. (78%) of trans-(±)-2-amino-6-cyano-5,5a,6,7,8,9,9a,10-octahydropyrimido[4,5-g]quinoline were obtained having the following physical characteristics. Mass spectrum, molecular ion at 229; infrared spectrum peaks at 3307.18, 3157.70, 2202.87, 1660.83, 1599.10, 1564.38, 1486.26.

Analysis Calculated: C, 62.86; H, 6.59; N, 30.54; Found: C, 63.18; H, 6.70; N, 30.24.

PREPARATION 4

Preparation of trans-(±)-2-amino-5,5a,6,7,8,9,9a,10-octahydropyrimido[4,5-g]quinoline A reaction mixture was prepared from 1.66 g. of the 6-cyano compound of Preparation 3, 9.7 g. of zinc dust, 200 ml. of acetic acid and 50 ml. of water. The reaction mixture was heated to reflux temperature under a nitrogen atmosphere for about 24 hours and then stirred at room temperature for a 48 hour period. Any volatile material was removed from the reaction mixture in vacuo and the resulting residue dissolved in water. The aqueous mixture was made basic with 50% aqueous sodium hydroxide. (eventual pH was in the range 10–11). A heavy white precipitate formed. The basic solution was filtered and the filtrate extracted three times with a 3:1 chloroform/isopropanol solvent mixture. The organic extracts were combined and dried. Removal of the solvent in vacuo yielded a light yellow powder comprising trans-(±)-2-amino-5,5a,6,7,8,9,9a,10-octahydropyrimido[4,5-g]quinoline free base. The free base was converted to the hydrochloride salt which was recrystallized from a methanol/acetate solvent mixture to yield crystalline material melting above 230° C.

Analysis (after drying at 150° C.) Calculated: C, 47.66; H, 6.55; N, 20.21; Found: C, 47.37; H, 6.65; N, 19.91.

Trans-(±)-2-amino-5,5a,6,7,8,9,9a,10-octahydropyrimido[4,5-g]quinoline thus prepared can be alkylated with a lower alkyl halide or allylated with an allyl halide to yield compounds coming within the scope of formula III above.

All of the above preparations were carried out with the racemate. It will be apparent to those skilled in the art that these same chemical steps can be carried out on the separated trans-(−) stereoisomer to yield optically active intermediates and final products.

As previously stated, the drugs of this invention as represented by formulas III and IV above are dopamine agonists without any other pronounced pharmacologic action. One of such dopamine agonist activities is the inhibition of prolactin secretion, as demonstrated according to the following procedure.

Adult male rats of the Sprague-Dawley strain weighing about 200 g. were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the test drug. The purpose of the reserpine was to keep the rat prolactin levels uniformly elevated. The compound was dissolved in 10 percent ethanol, and injected intraperitoneally at doses of 0.017, 0.03, 0.17 and 0.3 $\mu$ moles/kg. The compound was administered at each dose level to a group of 10 rats, and a control group of 10 intact males received an equivalent amount of 10 percent ethanol. One hour after treatment, all rats were killed by decapitation, and 150 $\mu$l aliquots of serum were assayed for prolactin.

The difference between the prolactin level of the treated rats and prolactin level of the control rats, divided by the prolactin level of the control rats gives the percent inhibition of prolactin secretion attributable to the given dose. Inhibition percentages are given in Tables 1 and 2 below for compounds according to III or IV above respectively. In the tables, columns 1 and 2 give substitution patterns for the basic structures at the head of the Table, column 3 the form (salt or free base—FB), and columns 4, 5, 6, and 7 the percent prolactin inhibition at the specified dose levels.

TABLE 1

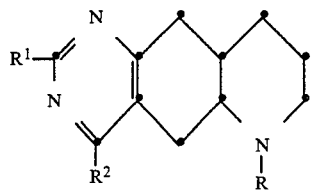

| R | R¹ | R² | Form | 100 μg/kg | 50 μg/kg | 10 μg/kg | 5 μg/kg | 1 μg/kg |
|---|---|---|---|---|---|---|---|---|
| CH₃ | NH₂ | H | 2HCl | — | 22 | 23 | — | — |
| n-C₃H₇ | NH₂ | H | 2HCl | 94 | 85 | 72 | — | 13 |
| n-C₃H₇ | C₆H₅CONH | H | FB | | 78 | 32 | — | — |
| n-C₃H₇ | CH₃CONH | H | FB | | 92 | 63 | — | — |
| n-C₃H₇ | (CH₃)₂N | H | 2HCl | | 81 | — | 21 | — |
| n-C₃H₇ | NH₂ | Cl | HCl | | 36 | | | |
| n-C₃H₇ | NH₂ | CH₃ | 2HCl | | 80 | | | |

TABLE 2

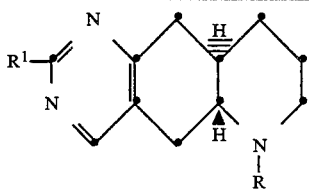

| R | R¹ | Form | 50 μg/kg | 10 μg/kg | 5 μg/kg | 1 μg/kg |
|---|---|---|---|---|---|---|
| n-C₃H₇ | NH₂ | 2HCl | 88, 94, 82 | 75 | 49, 58, 56 | 5 |

The compounds represented by III and IV are also active by the oral route, but at higher doses, i.e., 10 mcg. by the IP route gave a 75% inhibition but 50 mcg/kg a 91% inhibition by the oral route for trans-(±)-2-amino-6-n-propyl-5,5a,6,7,8,9,9a,10-octahydropyrimido[4,5-g]quinoline, dihydrochloride, and second compound in Table 1.

Compounds according to III and IV, dopamine agonists, have been found to affect turning behavior in 6-hydroxydopamine-lesioned rats in a test procedure designed to uncover compounds useful for the treatment of Parkinsonism. In this test, nigroneostriatal-lesioned rats are employed, as prepared by the procedure of Ungerstedt and Arbuthnott, *Brain Res*, 24, 485 (1970). A compound having dopamine agonist activity causes the rats to turn in circles contralateral to the side of the lesion. After a latency period, which varies from compound to compound, the number of turns is counted over a 15-minute period.

Results obtained from such testing are set forth in Table 3 below. In the table, columns 1 and 2 give the substitution pattern for the compound at the head of the table, column 3, percent of test animals exhibiting turning behavior, and column 4, average number of turns observed in first 15 minutes after end of latency period.

TABLE 3

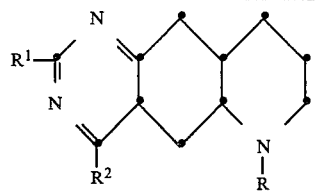

| | | | % of rats exhibiting turning behavior-dose in mcg/kg | | | | Average number of Turns per rat-dose in mcg/kg | | | |
|---|---|---|---|---|---|---|---|---|---|---|
| R | R¹ | R² | 1000 | 100 | 20 | 10 | 1000 | 100 | 20 | 10 |
| CH₃ | NH₂ | H | 100 | — | — | — | 38 | — | — | — |
| n-C₃H₇ | NH₂ | H | 100 | — | 94 | 50 | 62 | — | 54 | 41 |
| n-C₃H₇ | C₆H₅CO—NH | H | — | 60 | — | — | — | 51 | — | — |
| n-C₃H₇ | CH₃CO—NH | H | 80 | — | — | — | 42.5 | — | — | — |
| n-C₃H₇ | (CH₃)₂N | H | 100 | — | — | — | 40.5 | — | — | — |
| n-C₃H₇ | NH₂ | Cl | 83 | — | — | — | 49 | — | — | — |
| n-C₃H₇ | NH₂ | CH₃ | 100 | — | — | — | 46 | — | — | — |

5aR,9aR-2-amino-6-n-propyl-5,5a,6,7,8,9,9a,10-octahydropyrimido[4,5-g]quinoline given at a 100 mcg/kg dose produced an average 51 turns with 100% of the animals responding.

The drugs of this invention (III and IV) are also active in affecting turning behavior by the oral route, although somewhat higher doses are required to given significant effects.

The compounds of structures III and IV reduce the blood pressure of spontaneously hypertensive rats, as illuminated by the following experiment:

Adult male spontaneously hypertensive rats (SHR) (Taconic Farms, Germantown, N.Y.), weighing approximately 300 g. were anesthetized with pentobarbital sodium (60 mg./kg., i.p.). The trachea was cannulated and the SHR respired room air. Pulsatile arterial blood pressure was measured from a cannulated carotid artery using a Statham transducer (P23 ID). Mean arterial blood pressure was calculated as diastolic blood pressure plus ⅓ pulse pressure. Cardiac rate was monitored by a cardiotachometer which was triggered by the systolic pressure pulse. Drug solutions were administered i.v. through a catheter placed in a femoral vein. Arterial blood pressure and cardiac rate were recorded on a multichannel oscillograph (Beckman, Model R511A). Fifteen minutes were allowed to elapse following surgery for equilibration of the preparation.

Table 4 which follows gives the results of this test for trans-($\pm$)-2-amino-6-n-propyl-5,5a,6,7,8,9,9a,10-octahydropyrimido[4,5-g]quinoline. In Table 4, column 1 gives the dose level, column 2 the change in mean arterial blood pressure with standard error, and column 3, the percent change in cardiac rate with standard error.

TABLE 4

| Dose level in mcg/kg | Percent Changes* | |
|---|---|---|
| | Mean Arterial Blood Pressure** | Cardiac Rate |
| 0.1 | −4.0 ± 0.9 | −2.0 ± 0.4 |
| 1 | −14.8 ± 1.1 | −5.9 ± 0.8 |
| 10 | −46.5 ± 6.8 | −29.0 ± 2.3 |
| 100 | −37.1 ± 7.0 | −31.0 ± 4.2 |

*Change was measured immediately after injection. Baseline mean arterial blood pressure was 181 ± 1.0 mm Hg and mean cardiac rate was 366 ± 15 beats/min.
**Mean response for four SHR.

In addition, trans-($\pm$)-2-amino-6-n-propyl-5,5a,6,7,8,9,9a,10-octahydropyrimido[4,5-g]quinoline and its trans-($\pm$)-stereoisomer are potent activators of intensive cholinergic neurons in rat striatum leading to an elevation of striatal acetyl choline concentrations.

The compounds of this invention are administered for therapeutic purposes in a variety of formulations as illustrated below.

Hard gelatin capsules are prepared using the following ingredients:

| | Quantity (mg./capsule) |
|---|---|
| Active compound | .1-2 mg |
| Starch dried | 200 |
| Magnesium stearate | 10 |

The above ingredients are mixed and filled into hard gelatin capsules.

A tablet formulation is prepared using the ingredients below:

| | Quantity (mg./tablet) |
|---|---|
| Active compound | .1-2 mg |
| Cellulose, microcrystalline | 400 |
| Silicon dioxide, fumed | 10 |
| Stearic acid | 5 |

The components are blended and compressed to form tablets.

Alternatively, tablets each containing 0.1-2 mg. of active ingredient are made up as follows:

| Active ingredient | .1-2 mg. |
|---|---|
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets.

Capsules each containing 0.1-2 mg. of medicament are made as follows:

| Active ingredient | .1-2 mg. |
|---|---|
| Starch | 59 mg. |
| Microcrystalline cellulose | 59 mg. |
| Magnesium stearate | 2 mg. |

The active ingredient, cellulose, starch and magnesium stearate are blended, passed through a No. 45 mesh U.S. sieve, and filled into hard gelatin capsules.

Suspensions each containing 0.1-2 mg. of medicament per 5 ml. dose are made as follows:

| Active ingredient | .1-2 mg. |
|---|---|
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

For oral administration, tablets, capsules or suspensions containing from about 0.1 to about 2 mg. of active drug per dose are given 3-4 times a day, giving a daily dosage of 0.3 to 8 mgs. or, for a 75 kg person, about 4.0 to about 107 mcg/kg. The intravenous dose is in the range from about 0.1 to about 100 mcg./kg.

We claim:

1. A method of treating Parkinson's Syndrome consisting of administration to a mammal suffering from Parkinson's Syndrome and in need of treatment an effective dose of a drug of the formula

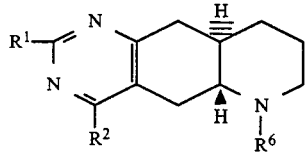

in which R¹ is NH₂, NHCH₃, N(CH₃)₂, NH—CO—CH₃ or NH—CO-phenyl, R² is H, Cl, Br or CH₃ and R⁶ is C₁₋₃ alkyl or allyl, or a pharmaceutically-acceptable addition salt thereof.

2. A method of inhibiting the secretion of prolactin in a mammal which consists of admnistering to a mammal having a physiologic condition characterized in part by elevated prolactin levels, an amount of a drug of the formula

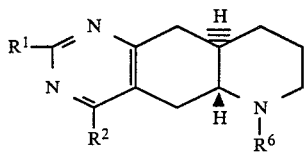

in which R¹ is NH₂, NHCH₃, N(CH₃)₂, NH—CO—CH₃ or NH—CO-phenyl, R² is H, Cl, Br or CH₃ and R⁶ is C₁₋₃ alkyl or allyl, or a pharmaceutically-acceptable acid additional salt thereof.

3. A method of treating hypertension in mammals which consists of administering to a hypertensive mammal a blood-pressure lowering dose of a compound of the formula

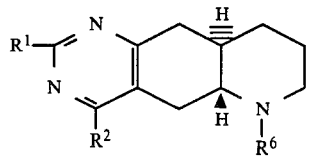

in which R¹ is NH₂, NHCH₃, N(CH₃)₂, NH—CO—CH₃ or NH—CO-phenyl, R² is H, Cl, Br or CH₃ and R⁶ is C₁₋₃ alkyl or ally, or a pharmaceutically-acceptable acid addition salt thereof.

4. A method of treating depression in mammals which consists of administering to a mammal in a depressed state, a depression alleviating dose of a compound of the formula

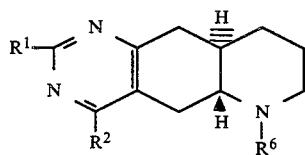

in which R¹ is NH₂, NHCH₃, N(CH₃)₂, NH—CO—CH₃ or NH—CO-phenyl, R² is H, Cl, Br or CH₃ and R⁶ is C₁₋₃ alkyl or allyl, or a pharmaceutically-acceptable acid addition salt thereof.

5. A method according to claim 1 in which trans-(—)-2-amino-6-n-propyl-5,5a,6,7,8,9,9a,10-octahydropyrimido[4,5-g]quinoline is administered.

6. A method according to claim 2 in which trans(—)-2-amino-6-n-propyl-5,5a,6,7,8,9,9a,10-octahydropyrimido[4,5-g]quinoline is administered.

7. A method according to claim 3 in which trans-(—)-2-amino-6-n-propyl-5,5a,6,7,8,9,9a,10-octahydropyrimido[4,5-g]quinoline is administered.

8. A method according to claim 4 in which trans-(—)-2-amino-6-n-propyl-5,5a,6,7,8,9,9a,10-octahydropyrimido[4,5-g]quinoline is administered.

* * * * *